United States Patent [19]

Belleau, deceased et al.

[11] Patent Number: 5,138,061

[45] Date of Patent: Aug. 11, 1992

[54] THIOACYLATING REAGENTS

[75] Inventors: Bernard Belleau, deceased, late of Westount, by Pierrette Belleau, executrix; Denis Brillon, Laval; Gilles Sauvé, Laval; Boulos Zacharie, Laval, all of Canada

[73] Assignee: BioChem Pharma Inc., Laval, Canada

[21] Appl. No.: 389,852

[22] Filed: Aug. 4, 1989

[51] Int. Cl.$^5$ .................. C07D 235/26; C07D 401/06; C07D 403/06

[52] U.S. Cl. .................................... 546/199; 548/305

[58] Field of Search .................. 548/305; 540/424; 546/199

[56] References Cited

U.S. PATENT DOCUMENTS 3,499,085  3/1970  Sasse et al. .......................... 548/305
3,901,909  8/1975  Naraynan et al. ................... 548/305

FOREIGN PATENT DOCUMENTS 0222283  5/1987  European Pat. Off. .

OTHER PUBLICATIONS

B. Belleau and G. Malek, "A New Convenient Reagent for Peptide Synthesis", J. Am. Chem. Soc., 90, pp. 1651–1652 (1968).
B. Belleau et al., "Some Remarkable Effects of Thiopeptide and Derived Linkages on Lysozyme Release from Neutrophils by Esters of the Chemotactic Peptide N-Formyl-Methionyl-Leucyl-Phenylalanine (f-Met-Leu-Phe-OR)", Int. J. Immunopharmac., 11, pp. 467–471 (1989).
S. Salvadori et al., "Opioid Peptides. Structure-Activity Relationships of Dermorphin Endothiotetrapeptides", Farmaco Ed. Sci., 39 (4), pp. 316–321 (1984).
D. W. Brown et al., "Mono- and Dithionopeptide Synthesis" Tetrahedron Letters, 28 (19), pp. 2171–2174 (1987).
K. Clausen et al., "Synthesis of Leucine Enkephalin and Aspartame Analogs Containing Thioamide Linkages at Specific Positions", Pept. Proc. Eur. Pept. Symp. (17th), pp. 207–210 (1982).
K. Clausen et al., "Role of the Peptide Backbone in Biological Activity: Synthesis of Enkephalins with Psi (CH$_2$S) and Psi (CSNH) Amide Bond Replacements", Pept.: Struct. Funct. Proc. Am. Pept. Symp. (8th), pp. 307–310 (1983).
W. L. Mock et al., "Hydrolysis of a Thiopeptide by Cadmium Carboxypeptidase A.", Biochem. Biophys. Res. Commun., 102 (1), pp. 389–396 (1981).
A. R. Katrinsky et al., "Azlactones as Polymer Components and Intermediates", J. Polym. Sci. Polym. Chem. Ed., 27 (5) pp. 1781–1790 (1989).
D. B. Sherman et al., "Compatibility of Thioamides With Reverse Turn Features: Synthesis and Conformational Analysis of Two Model Cyclic Pseudo-Peptides Containing Thioamides As Backbone Modifications", J. Am. Chem. Soc., 112 (1) pp. 433–441 (1990).
O. K. Archer et al., "Reduced Antibody Response In Thymectomized Rabbits", Nature, 195, pp. 191–193 (1962).
P. A. Bartlett et al., "A Thioamide Substrate Of Carboxypeptidase A", Biochemistry, 21, pp. 1608–1611 (1982).
P. Campbell and N. T. Nashed, "Carboxypeptidase A Catalyzed Hydrolysis Of Thiopeptide And Thionester Analogues Of Specific Substrates, An Effect On k$_{cat}$ For Peptide, But Not Ester Substrates", J. Am. Chem. Soc., 104, pp. 5221–5226 (1982).
K. Clausen et al., "Evidence Of A Peptide Backbone Contribution Toward Selective Receptor Recognition For Leucine Enkephalin Thioamide Analogs", Biochem. Biophys. Res. Comm., 120, pp. 305–310 (1984) (Clausen I).
K. Clausen et al., "Studies On Amino Acids And Peptides. Part 6. Methods For Introducing Thioamide Bonds Into The Peptide Backbone: Synthesis Of The Four Monothio Analogues Of Leucine Enkephalin", J. Chem. Soc. Perkin Trans. I, pp. 785–798 (1984) (Clausen II).
G. Lajoie et al., "Synthesis And Biological Activity Of Monothionated Analogs Of Leucine-Enkephalin", Int. J. Pept. Prot. Res., 24, pp. 316–327 (1984).
C. Y. Lau and G. Goldstein, "Functional Effects Of Thymopoietin$_{32-36}$ (TP5) On Cytotoxic Lymphocyte Precursor Units (CLP-U). I. Enhancement of Splenic CLP-U In Vitro and In Vivo After Suboptimal Antigenic Stimulation", J. Immunol., 124, pp. 1861–1865 (1980).
L. Maziak et al., "Productive Conformation In The Bound State And Hydrolytic Behavior Of Thiopeptide Analogues Of Angiotensin-Converting Enzyme Substrates", J. Am. Chem. Soc., 108, pp. 182–183 (1986).
R. B. Merrifield, "Solid Phase Peptide Synthesis. I. The Synthesis Of A Tetrapeptide", J. Am. Chem. Soc., 85, pp. 2149–2154 (1963).
D. Osoba and J. F. A. P. Miller, "Evidence For A Humoral Thymus Factor Responsible For The Maturation of Immunological Faculty", Nature, 199, pp. 653–654 (1963).
G. E. Ranges et al., "T Cell Development In Normal And Thymopentin-Treated Nude Mice", J. Exp. Med., 156, pp. 1057–1064 (1982).
W. Ried and E. Schmidt, "N-Acylierte α-Aminoimidsäureester, Iminodipeptide Und Endothiodipeptide", Liebigs Ann. Chem., 695, pp. 217–225 (1966).
W. Ried and W. von der Emden, "Aminosaure-Thionester Und Endothiopeptide, II", Liebigs Ann. Chem., 642, pp. 128–133 (1961).

Primary Examiner—Robert W. Ramsuer
Assistant Examiner—M. S. H. Gabilan
Attorney, Agent, or Firm—James F. Haley, Jr.; Leslie A. McDonell

[57] ABSTRACT

Thioacylating reagents are provided for the introduction of thioamide bonds into growing peptides represented by the structure:

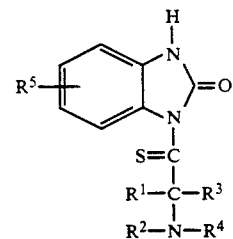
where the substituents are disclosed herein. Intermediate precursors for preparing these thioacylating reagents are also provided. A process for preparing the thioacylating reagents and the intermediate precursors is further provided.
11 Claims, No Drawings

THIOACYLATING REAGENTS

TECHNICAL FIELD OF THE INVENTION

This invention relates to novel α-amino acid derivatives used as thioacylating reagents, intermediates formed as precursors to these derivatives, thiopeptides of biological and medicinal importance prepared through the use of these thioacylating reagents which introduce thioamide linkages into the growing peptide, and their methods of production. The thiopeptides disclosed herein are characterized by providing superior activity in vivo as biological response modifiers, neuroeffectors, immunomodulators and the like and by increased resistance to enzymatic degradation due to the introduction of a thioamide linkage into the backbone of the peptide. The thiopeptides are described herein as peptides which contain a thioamide linkage between adjacent amino acid residues. At least one such substitution by a sulphur atom of an oxygen atom in the amide bond of the backbone of the peptide structure is desired. As will be appreciated by the disclosure to follow, the thioacylating reagents may be used to introduce this thioamide linkage into a growing peptide with relative ease and in substantially higher yields than observed in prior processes while retaining the optical integrity of the peptide. The phrase growing peptide signifies that amino acid chain elongation is occurring which increases the size of the peptide by incorporating additional residues into the peptide sequence.

BACKGROUND OF THE INVENTION

The number of biologically active peptides is quite large. However, their potential utility as response modifiers, neuroeffectors or immunomodulators is dramatically circumscribed by their demonstrated very short half-lives in vivo and their lack of effectiveness when administered orally. This latter phenomenon is primarily due to the extreme ability of biologically active polypeptides in the presence of the peptidases and proteases normally found in the digestive tract.

It is desirable to stabilize the backbone amide linkages of these biologically active peptides against such proteolytic enzymes in order to improve the pharmacokinetic properties of these peptides. Enhanced stability to enzymatic degradation would make these peptides more useful therapeutic agents.

Recent advances in chemical replacement or modification of peptide linkages indicate that such linkage stabilization is feasible. By replacement of peptide linkages with thioamide bonds at those positions of the peptide backbone responsible for the biological response-limiting cleavage by peptidases and proteases, an increased stability to enzymatic degradation is obtained for many thiopeptide analogs. Reid and von Der Emden (W. Reid and W. von Der Emden, "Aminosaure-thionester und Endothiopeptide, II", *Liebigs Ann. Chem.*, 642, 128, (1961)) discuss racemic thioamide formation through the thionester thioacylating agent:

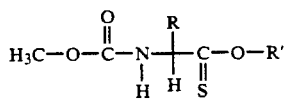

wherein R and R' are selected from lower alkyl and aryl. Further, enhanced pharmacological activity is exhibited for many of these analogues. Lajoie, et al., (G. Lajoie, F. Lepine, S. LeMaire, F. Jolicoeur, C. Aube, A. Turcotte and B. Belleau, "Synthesis and Biological Activity of Monothionated Analogs of Leucine-enkephalin", *Int. J. Pept. Protein Res.*, 24, 316, (1984)). Thiopeptide derivatives have demonstrated increased activity in vivo as biological response modifiers, neuroeffectors, and immunomodulators as compared with their oxygenated analogs. For example, Causen, et al. (K. Clausen, A. Spatola, C. Lemieux, P. Schiller, and S. Lawesson, "Evidence of a Peptide Backbone Contribution Toward Selective Receptor Recognition for Leucine Enkephalin Thioamide Analogs", *Biochem. Biophys. Res. Commun.*, 120, 305, (1984)) demonstrate the increased pharmacological activity of one such thiopeptide analog over its oxygenated counterpart.

Methods for replacement for the carbonyl oxygen atom of a carboxyl moiety with a sulphur atom are known. Clausen, et al. (K. Clausen, M. Thorsen, and S. Lawesson, "Studies on Amino Acids and Peptides. Part 6. Methods for Introducing Thioamide Bonds into the Peptide Backbone: Synthesis of the Four Monothio Analogues of Leucine Enkephalin", *J. Chem. Soc. Perkin Trans.*, 785, (1984)) describe thioacylation by the use of dithioesters of the formula:

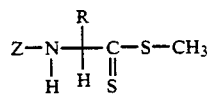

wherein Z is carbobenzoxy and R is selected from hydrogen, lower alkyl, and aryl. No information, however, regarding racemization is described. It is also known that the thiopeptides so formed are useful reagents and intermediates for further thiopeptide synthesis. See, P. Campbell, and N. Nashed, "Carboxypeptidase A Catalyzed Hydrolysis of Thiopeptide and Thionester Analogues of Specific Substrates. An Effect on $K_{cat}$ for Peptide, but not Ester, Substrates", *J. Am. Chem. Soc.*, 104, 5221-26, (1982); P. Bartlett, K. Speer, and N. Jacobsen, "A Thioamide Substrate of Carboxypeptidase A", *Biochemistry*, 21, 1608-11, (1982); and L. Maziak, G. Lajoie, and B. Belleau, "Productive Conformation in the Bound State and Hydrolytic Behavior of Thiopeptide Analogues of Angiotensin-converting Enzyme Substrates", *J. Am. Chem. Soc.*, 108, 182-83, (1986). Such thiopeptide derivatives also have shown resistance to enzymatic hydrolysis. W. Reid and E. Schmidt, "N-acylierte α-Aminoimidosaureester, Imidodipeptide and Endothiodipeptide", *Liebigs Ann. Chem.*, 695, 217, (1966), for example, disclose the synthesis of a protected amino acid thionester as an intermediate in the preparation of a thiopeptide in moderate yield.

Thionation of peptides, or the replacement of an oxygen atom with a sulphur atom, at the carbonyl functionality of their peptide bonds has heretofore demonstrated a lack of reaction site specificity. Decreased overall yields have been observed because of side reactions and the by-products so formed which cause the purity of the product and the efficiency of the reaction to suffer. Further, the optical integrity of the final product is often not maintained due to the reaction mechanism of the previously used thioacylating reagents. The limited effectiveness of these thioacylating reagents severely circumscribed the potential of thiopeptides as pharmacological agents. Lack of an efficient method of producing pure, optically active thiopeptides has rendered the evaluation of pharmacological activity, stability to enzymatic and pH degradation, and toxicity of such compounds very difficult, since sufficient quantities of these materials have heretofore been unobtainable.

The optical integrity of a compound relates to its ability to rotate light. This ability is measured in an instrument known as a polarimeter which utilizes a zero point reference. The degree to which a chemically pure material rotates light indicates its relative optical purity. That is, a material may be chemically pure while being optically inactive or racemic. The amount of activity that is observed from a material is often dependent upon its optical purity. Two enantiomers although possessing idential chemical formulae may have completely different biological activities. It is common in medicinal applications for a compound of one optical configuration to exhibit activity and usefulness, while its optical rotamer or complementary enantiomer demonstrates a different activity or is wholly inert. Thus, where optical configuration is important, optical purity, as well as chemical purity, is an important concern.

It is desirable that a thiopeptide meet several criteria to be suitable for pharmacological study. First, the thiopeptide should demonstrate an increased resistance to enzymatic degradation. Second, the thiopeptide should elicit an enhanced biological response over its oxygenated counterpart. Third, it must be safe for human ingestion. Fourth, the thiopeptide should be capable of being produced in quantities large enough to perform clinical studies.

Regardint he first three concerns, the characteristics described should be possessed as inherent properties of the thiopeptide which establish it as superior to other peptides not containing a thioamide linkage between adjacent amino acid residues. With reference to the last criterion, it is advantageous to be capable of producing large quantities of material. Several factors are important with respect to this consideration. The process for producing the thiopeptide is preferably simple, efficient and economical. That is, the reaction scheme of the process should contain few steps, afford high overall yields, and demonstrate minimal by-product formation. Moreover, the scheme should preferably utilize inexpensive reagents and materials. Further, the method should ensure the optical integrity of the growing peptide by avoiding reations that will reacemize the compound. That is, a racemic mixture is likely not to fully exhibit the desired pharmacological response.

Prior thioacylation processes have suffered from being cumbersome and complicated, Moreover, they do not afford products with a high degree of optical integrity and provide inadequate overall yields of the thiopeptide.

Accordingly, there is a need for thioacyclating reagents which permit the selective incorporation of thioamide linkages into growing peptides at specific residue linkages while utilizing efficient reaction conditions. There is also a need for a thioacylation process which will retain the optical integrity of the resulting peptide and will produce such peptide in high yields. There is additionally a need for methods for preparing thioacylating reagents capable of simple and economical reaction with amino acids and peptides to produce thiopeptides. There is yet another need for thiopeptides, and methods to prepare them, having increased enzymatic stability and enhanced biological activity over their oxygenated analogs.

SUMMARY OF THE INVENTION

It is an object of this invention to provide thioacylating reagents. It is also an object of this invention to provide thioacylating reagents which will introduce thioamide linkages into growing peptides in high yield. It is a further object of this invention to provide thioacylating reagents which will retain the optical integrity of the peptide so formed. It is another object of this invention to provide novel intermediates to prepare the thioacylating reagents. It is yet another object of this invention to provide thiopeptides which demonstrate greater pharmacological effectiveness with respect to activity and resistance to degradation than their oxygenated analogs. It is still another object of this invention to provide methods for synthesizing these thioacylating agents, novel intermediates, and thiopeptides.

These and other objects are achieved herein by thioacylating reagents represented by the formula:

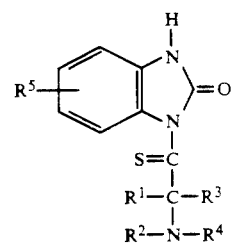

wherein $R^1$ is hydrogen, $C_1$–$C_4$ branched or unbranched alkyl which may or may not be substituted by

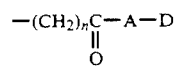

(a)

wherein
A is —O— or —NH—,
D is benzyl or xanthyl,
n is 1 or 2;

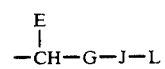

(b)

wherein
E is —H or —CH$_3$,
G is —CH$_2$—, —O— or —S—,
J is —S— or —CH$_2$—,
L is —CH$_3$ or phenyl;

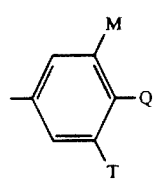

(c)

wherein M and T may be the same or different and are selected from hydrogen, fluorine, chlorine, bromine and iodine and Q is hydrogen, hydroxy, or dichlorobenzoxy (2ClZ);

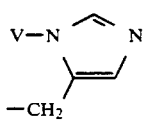

wherein V is carbobenzoxy or tosyl; or

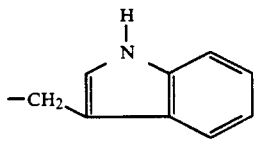

$R^2$ is selected from t-butoxycarbonyl, carbobenzoxy, chlorobenzyloxy, 9-fluorenylmethyloxycarbonyl, tosyl, trityl or xanthenyl;

$R^3$ is selected from hydrogen, methyl or ethyl; or $R^1$ and $R^3$, taken together with the carbon atom to which they are attached, form a saturated hydrocarbon ring containing 3–5 carbon atoms;

$R^4$ is hydrogen: or $R^1$ and $R^4$, taken together with the carbon and nitrogen atoms to which they are attached, form a saturated heterocycle containing 2–6 ring carbon atoms (i.e., an aziridine, azetidine, pyrrolidine, or piperidine ring); and $R^5$ is selected from hydrogen, fluorine, chlorine, bromine, iodine, amido, amino, carboxyl, carboxymethyl, cyano, guanido, hydroxyl, hydroxymethyl, mercapto, or nitro.

This invention also provides novel intermediate compounds that are extremely well suited for preparing the thioacylating reagent of this invention.

This invention additionally provides thiopeptides that exhibit increased resistance to enzymatic degradation and demonstrate enhanced biological activity in vivo over their oxygen containing counterparts.

This invention further provides methods for synthesizing these thioacylating reagents and novel intermediates useful in the preparation of these reagents, as well as processes for producing the thiopeptides represented herein.

In accordance with this invention, we provide a class of reagents for thioacylation that may introduce thioamide linkages into peptides or other suitable compounds in a simple, efficient, economical manner and in high yield. Thioacylation carried out using these reagents will furthermore maintain the optical integrity of the newly formed compound.

Also in accordance with this invention, we provide a method of producing these reagents and provide novel intermediates useful in the preparation of the thioacylating reagent.

In accordance with another aspect of this invention, we provide a series of thiopeptides which demonstrate an increased resistance to enzymatic degradation and an enhanced pharmacological activity as compared with corresponding peptides containing only amide bonding between adjacent residues. These thiopeptides show utility as biological response modifiers, neuroeffetors, immunomodulators and the like.

In accordance with this aspect of the invention, the thiopeptides are represented by the formula:

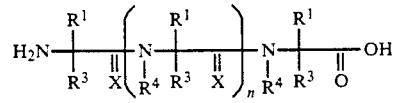

and salts thereof, wherein $R^1$ is hydrogen, $C_1$-$C_4$ branched or unbranched alkyl which may or may not be substituted by

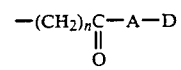     (a)

wherein
A is —O— or —NH—,
D is benzyl or xanthenyl,
n is 1 or 2;

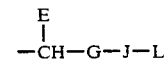     (b)

wherein
E is —H or —$CH_3$,
G is —$CH_2$—, —O— or —S—
J is —S— or —$CH_2$—,
L is —$CH_3$ or phenyl;

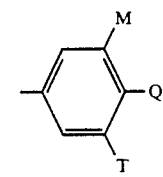     (c)

wherein M and T may be the same or different and are selected from hydrogen, fluorine, chlorine, bromine and iodine and Q is hydrogen, hydroxy or 2ClZ;

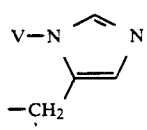     (d)

wherein V is carbobenzoxy or tosyl; or

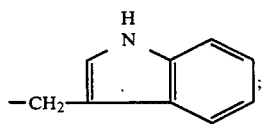     (e)

$R^3$ is selected from hydrogen, methyl or ethyl;
$R^1$ and $R^3$, taken together with the carbon atom to which they are attached, form a saturated hydrocarbon ring containing 3–5 carbon atoms;
$R^4$ is hydrogen or $R^1$ and $R^4$, taken together with the carbon and nitrogen atoms to which they are attached, for a saturated heterocycle containing 2–6 ring carbon atoms (i.e., an aziridine, azetidine, pyrrolidine, or piperidine ring); and n is 1–4.

DETAILED DESCRIPTION OF THE INVENTION

Thioacylating Reagents

In accordance with the present invention, the thioacylating reagents are represented by:

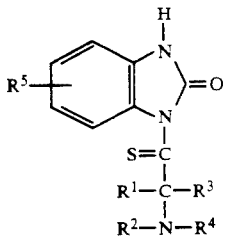
(III)

wherein $R_1$ is represented by a member of the group consisting of hydrogen, $C_1$-$C_4$ branched or unbranched alkyl which may or may not be substituted by a member selected from the group consisting of:

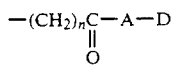
(a)

wherein
A is —O— or —NH—,
D is benzyl or xanthenyl,
n is 1 or 2;

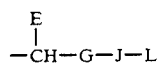
(b)

wherein
E is —H or —CH$_3$,
G is —CH$_2$—, —O— or —S—,
J is —S— or —CH$_2$—,
L is —CH$_3$ or phenyl;

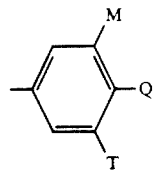
(c)

wherein M and T may be the same or different and are selected from hydrogen, fluorine, chlorine, bromine and iodine and Q is hydrogen, hydroxy or 2ClZ;

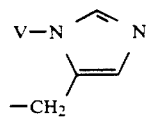
(d)

wherein V is carbobenzoxy or tosyl; or

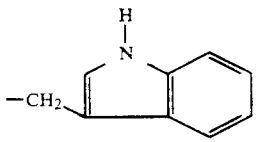
(e)

$R^2$ is represented by a member selected from the class consisting of:

t-butoxycarbonyl, carbobenzoxy, chlorobenzyloxy, 9-fluorenylmethyloxycarbonyl, tosyl, trityl or xanthenyl;

$R^3$ is selected from hydrogen, methyl or ethyl; or $R^1$ and $R^3$, taken together with the carbon atom to which they are attached, form a saturated hydrocarbon ring containing 3-5 carbon atoms;

$R^4$ is hydrogen; or $R^1$ and $R^4$, taken together with the carbon and nitrogen atoms to which they are attached, form a saturated heterocycle containing 2-6 ring carbon atoms (i.e., an aziridine, azetidine, pyrrolidine, or piperidine ring); and $R^5$ is selected from hydrogen, fluorine, chlorine, bromine, iodine, amido, amino, carboxyl, carboxymethyl, cyano, guanido, hydroxyl, hydroxymethyl, mercapto, or nitro.

$R^1$ are typically substituents commonly found among natural α-amino acids. Particularly preferred groups include branched or unbranched alkyl groups which may or may not be substituted by amino, carboxy, guanido, hydroxy, hydroxymethyl or hydroxyphenyl.

The term thioacylating reagent is meant to include compounds which react with hydroxy and amino groups to introduce a thioacyl group to the nucleophilic substituent and becomes covalently bound thereto. The inclusion of thiocarbonyls in the amide bonds of peptides results in an increased resistance to hydrolysis and enzymatic destruction as compared with peptides of the same general structure but having conventional carbonyl moities in their amide linkages.

The amino acid ortho amino thioanilides of this invention are represented by:

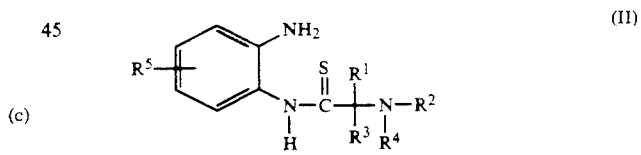
(II)

wherein $R^1$, $R^2$, $R^3$, $R^4$ and $R^5$ in the compound are as defined hereinabove. Preferred values for $R^1$ in these thioanilide intermediates are substituents commonly found among natural α-amino acids. Particularly preferred groupings include branched or unbranched alkyl groups that may or may not be substituted by amino, carboxy, guanido, hydroxy, hydroxymethyl or hydroxyphenyl.

The term amino acid ortho amino thioanilide is meant to include compounds having an ortho disubstituted amino benzene structure and an amino acid bound to said ortho disubstituted amino benzene structure by a thioamide linkage with said amino acid suitably protected at the amino terminus with an appropriate protecting group as defined for $R^2$ hereinabove.

The amino acid ortho amino anilides of this invention are represented by:

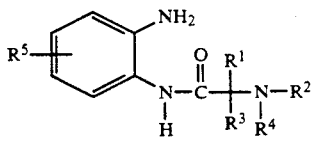

wherein $R^1$, $R^2$, $R^3$, $R^4$ and $R^5$ in the compound are as defined hereinabove. Preferred values for $R^1$ are those substituents commonly found among natural α-amino acids. Particularly preferred groupings include branched or unbranched alkyl groups which may or may not be substituted by amino, carboxy, guanido, hydroxy, hydroxymethyl or hydroxyphenyl.

The term amino acid ortho amino anilide is meant to include compounds having an ortho disubstituted amino benzene structure and an amino acid bound to one of the amino substitutents on said ortho disubstituted amino benzene structure through an amide linkage with said amino acid suitably protected at the amino terminus with an appropriate protecting group a defined for $R^2$ hereinabove.

The thioacylating reagents of the present invention may be prepared by initial reaction of an ortho-phenylenediamine conveniently with an amino acid according to the following scheme:

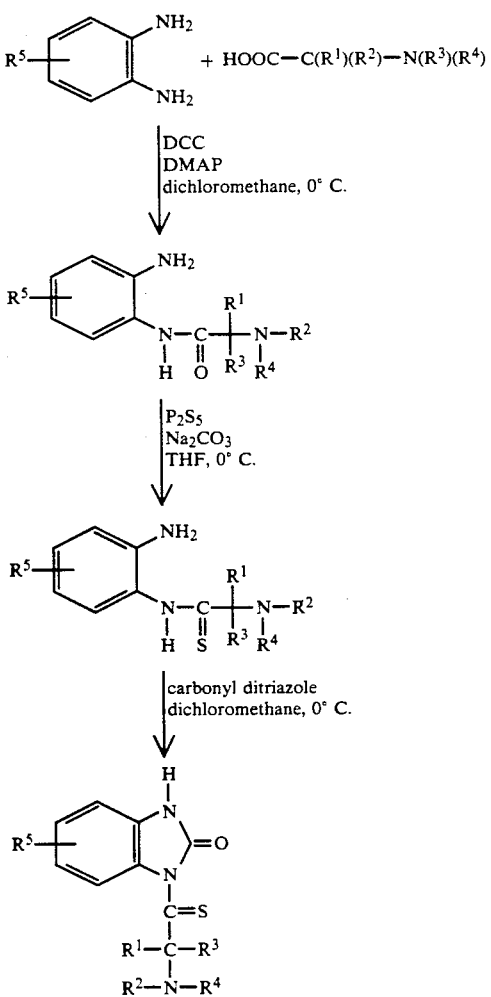

wherein $R^1$, $R^2$, $R^3$, $R^4$ and $R^5$ are as defined hereinabove.

Ortho-phenylene diamine and amino acids described herein may be reacted in the presence of a peptide coupling agent in a suitable solvent with stirring or agitation to form amino acid ortho amino anilides I. surprisingly, however, selective amide formation occurs at only one of the two amino substituents on the benzene ring. Contacting compounds of general formula I with a thionation a reagent in the presence of a suitable solvent at −78° C. to 0° C. with stirring or agitation forms amino acid ortho amino thioanilides II. Subsequent treatment of compounds of general formula II with a reagent well-suited to effect internal ring closure in a suitably inert solvent with stirring or agitation yields the desired compound of general formula III. The reaction scheme to form the thioacylating reagents is illustrated hereinabove.

The process of peptide synthesis requires specific functional groups to react with other substituents to link amino acid residues in a desired manner to form a peptide with a sought after and known sequence. Since amino acids possess at least two reactive substitutents, the amine and carboxylic acid portions, suitable protection or blocking of these functionalities is required to ensure that reaction will occur only at desired sites.

These protecting groups should be introduced to the moiety efficaciously while their removal should be performed under conditions which do not effect other portions of the molecule. In this manner, certain reactions and modifications may be performed on the amino acid, peptide, or other compound with assurance that the protected functionality will not interfere with the desired reaction. Further, by choosing a protecting group that is sensitive and labile to certain reactive conditions, a reaction scheme may be outlined to advantageously utilize these characteristics to effectively remove the protecting group once the synthesis is complete.

A variety of protecting groups known in the field of peptide synthesis and recognized by conventional abbreviations therein, may be found in T. Greene, Protective Groups In Organic Synthesis, Academic Press (1981). Among the preferred protecting groups that may be utilized for suitable protection of reactive nucleophilic substituents of $R^1$ are benzyl, carbobenzoxy or xanthenyl and for $R^2$ t-butoxycarboxyl or carbobenzoxy.

Coupling of ortho-phenylene diamine with amino acids as described above to yield compounds of general formula I may be accomplished employing established techniques in the field of peptide chemistry. A broad range of suitable reactions are described in E. Gross & J. Meinhofer, 4 The Peptides: Analysis, Synthesis, Biology; Modern Techniques of Peptide and Amino Acid Analysis, John Wiley & Sons, (1981) and M. Bodanszky, Principles Of Peptide Synthesis, Springer-Verlag (1984). The peptide coupling agents which may be used to assist condensation of amino and carboxylic acid moieties include N,N'-dicyclohexylcarbodiimide (DCC), N,N'-carbonyl diimidazole (CDI), 1-hydroxy benzotriazole (HOBt), ethyl chloroformate, and the like. A preferred technique uses DCC as the coupling reagent. The DCC method may be used with or without catalytic additives such as 4-dimethylaminopyridine (DMAP), copper (11) chloride or HOBt to hasten the reaction and suppress the racemization of the desired compound.

The DCC reaction is often performed at room temperature but may be performed from about −78° C. to gentle reflux in a variety of solvents that are inert with respect to the reactants. The solvents are normally organic solvents which are polar and aprotic. Preferred solvents include dichloromethane, chloroform, diethyl ether, tetrahydroform (THF), N,N'-dimethylformamide (DMF), and the like. Particularly preferred solvents are dichloromethane and DMF. In general, the coupling reaction may be carried out at atmospheric pressure at a temperature of −78° C. to reflux for a period of about 1-48 h. Preferably, the reaction is carried out at −10° C. to 25° C. with stirring, shaking or agitation over a period of 4-6 h.

Compounds of general formula 11 are typically prepared under anhydrous conditions, by reacting compounds of general formula I with a mixture of phosphorous pentasulfide and anhydrous sodium carbonate in an inert solvent. The reaction temperature is preferably about 0° C., but may then be varied from −78° C. to gentle reflux. The solvent is preferably anhydrous THF, and other suitable solvents include dichloromethane, diethyl ether, DMF, and the like.

Compounds of general formula III may be prepared by contacting compounds of general formula II with carbonyl ditriazole or phosgene in an inert solvent at a temperature of −78° C. to gentle reflux, preferably room temperature. The solvent may be selected from, but is not limited to, dichloromethane, diethyl ether, DMF and THF.

In any of the synthesis methods described above, the desired products may be isolated from the reaction mixture by crystallization. Alternatively, chromatographic techniques including, but not limited to, normal phase, reverse-phase, ion-exchange, affinity, or gel permeation, may be employed, as well as electrophoresis or extraction or other means.

Thiopeptides

A novel class of thiopeptides contemplated by the present invention may be represented by the following formula:

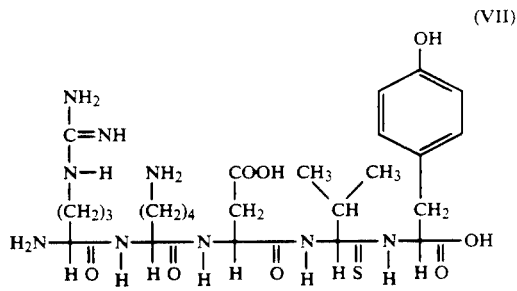

wherein X is S or O with at least one X being S, $R^1$, $R^2$, $R^4$ are as defined above, and n is 1-4. Preferred classes of thiopeptides are represented by the peptides comprising the following sequences:

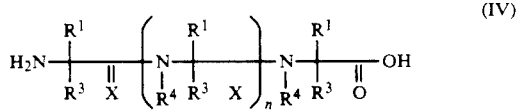

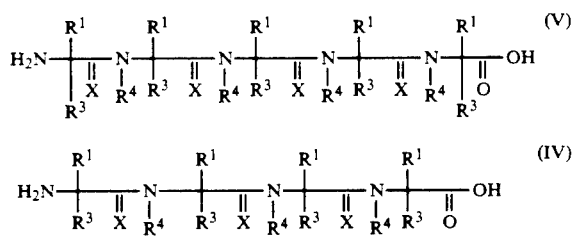

wherein X, $R^1$, $R^3$, and $R^4$ are as defined above.

For compounds of formula V, the peptides may have four, three, or two thiocarbonyl moieties, but most preferably there will be one thiocarbonyl with the remaining values represented by X being oxygen. A particularly preferred thiopeptide of formula V for enhanced stability and increased pharmacological activity is represented by formula VII:

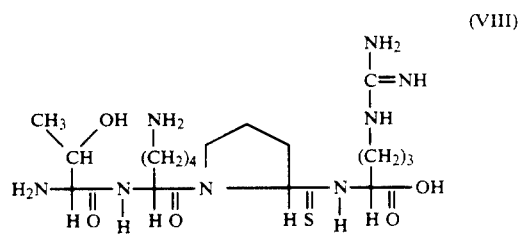

Similarly, for tetrapeptides of formula VI, especially preferred embodiments will be those wherein only one X represents a sulphur atom and the remaining two values for X each represent an oxygen atom. A most preferred series of thiopeptides of formula VI having increased resistance to enzymatic degradation and enhanced biological activity is represented by formula VIII:

The incorporation of thioamide linkages at positions on the peptide backbone which are susceptible to degradation may be performed in order to increase the peptide's resistance to enzymatic digestion. This enhanced stability may afford greater biological activities to the peptides prolonged existence. For example, thymopentin, which is merely a biologically active fragment of the polypeptide thymopoietin, may be modified to elicit this response. One such thymopentin derivative, 4-thio-thymopentin, represented by formula VII, has exhibited approximately a three-fold increase in biological activity. A control group of nude athymic mice was administered 20 micrograms of thymopentin per subject according to well-known assay techniques. See, e.g., O. Archer, T. Pierce, B. Papermanter, and R. Good, "Reduced Antibody Response in Thymectomized Rabbits", Nature, 195, 191 (1962); D. Oscaba and J. Miller, "Evidence for a Humeral Thymus Factor Responsible for the Maturation of Immunological Faculty", Nature, 199, 653 (1963); P. Magrit, "T-Cell Development in Normal and Thymopentintreated Nude Mice", J. Exp. Med., 156, 1057 (1982). The results of this assay showed a mean increase of 43% for the maturation of T cells and related immune responses. However, when the mice of the test group were administered the same dosage under the same assay conditions, a mean increase of 128% for T cell maturation was observed. Thus, the increased effect in potency confirms that the introduction of a sulphur atom as a replacement for the carbonyl oxygen atom of an amide bond may decrease the rate of enzymatic degradation, enhance the affinity for relevant receptors, or act to assist both phenomena.

Other peptides that may be modified to incorporate thiamide linkages into the peptides backbone according to the thioacylation technology of the present invention include, but are not limited to, Vasopressin (9 amino acid residues), Somatostatin (14 amino acid residues), α-Melanotropin (13 amino acid residues), Leutienizing Hormone Releasing Hormone (LHRH, 10 amino acid residues), Adrenocorticotropin (ACTH, 39 amino acid residues), β-Endorphin (31 amino acid residues), and Atrial Natriuretic Factor (ANF, 33 amino acid residues).

Site specific and mild conditions which assist in the efficient introduction of a thioamide linkage to the backbone of a growing peptide chain may be accomplished in high yield by the use of 1-thioacyl-2-benzimidazolones as thioacylating reagents according to this invention. The resulting thiopeptides demonstrate increased stability and greater pharmacological potency while retaining the optical integrity of their component amino acid residues.

The thioacylation agents of the present invention permit the formation of thioamide linkages in growing peptides in substantially higher yields over those methods of thioamide introduction previously reported. The methods of the present invention yield thiopeptides that demonstrate previously unknown stability with respect to resistance to enzymatic degradation. Further, the thiopeptides of this invention exhibit a substantial increase in pharmacological activity over peptide analogs that are linked by amide bonding between residues.

According to his invention, a thioamide moiety may be introduced into a growing peptide at a specific site in the peptide sequence by reacting a thioacylating reagent according to the invention with an amino acid or peptide. The peptide amino terminus must be protected at the terminal amino functionality. The reaction is advantageously carried out in a suitable solvent inert to the reactants in the presence of an appropriate peptide coupling reagent. The preferred solvents include dichloromethane, chloroform, diethyl ether, THF, DMF, and the like. Particularly preferred solvents are dichloromethane and DMF. The preferred reaction conditions are from −78° C. to gentle reflux for a period of about 1–48 h. Particularly preferred conditions are −10° C. to 25° C. stirring for a period of 4–6 h.

Until the thioamide linkage is required to be introduced, the peptide may be synthesized under any peptide coupling conditions. Alternatively, the thioamide linkage may be introduced first and the thiodipeptide so formed may then be enlarged employing generally recognized peptide coupling conditions Once the incorporation of the thioamide linkage is completed, and the thiopeptide is prepared, the compound so formed may be entirely freed of its protecting groups according to well-known protocols such as treatment with liquid hydrogen fluoride (HF). Where, however, the peptide or thiopeptide formed requires selective removal of the protective groups, usually from an amino terminus, suitable reaction conditions must be employed.

The t-butoxycarboxyl (Boc) protected amino functionality of amino acid derivatives and terminal amines of peptides may be removed, e.g., by treatment with cold trifluoroacetic acid (TFA) at 0° C. under suitable atmospheric conditions, e.g. adjusting the pH to about 8-9. The TFA salt of the amino acid derivative or protected peptide may be mixed in a suitable organic solvent and subjected to mild aqueous basic conditions. The organic solution, containing said amino acid derivative or said protected peptide with free amino functionality, may then be dried and concentrated to afford the free amino derivative.

In the case of 9-fluorenylmethyloxycarbonyl (Fmoc) protected amino acids, thiopeptides or Merrifield resin derivatives are presented, the corresponding free amino group may be generated selectively by treatment with piperidine in DMF under suitable atmospheric and thermal conditions.

An alternative synthetic approach for introducing thioamide linkages can be effectuated via the Merrifield solid phase methodology and its known variants. Thus, a Merrifield resin is prepared by well-known solid phase peptide synthesis methods. A covalently attached α-amino acid residue, attached at its carboxyl function or, similarly, a peptide with a free terminal amino functionality is carried by said resin. Treatment of said resin with said thioacylating reagent under standard solid phase peptide synthesis conditions affords the desired product.

Where this process introduces the thioamide linkage as the final step of thiopeptide formation, the thiopeptide may be liberated from said resin by using well-established methods. By employing liquid-HF containing dialkyl sulfide with anisole and thioanisoe under suitable conditions at a temperature of −78° C. to 0° C., the thiopeptide may be obtained free from all of the individual protecting groups of the component amino acid residues.

The amounts of the reactants utilized in the aforementioned reaction may vary widely and the conditions required to facilitate reaction and encourage efficient completion may also vary widely. However, in general, the amounts of material employed to induce reaction in the processes discussed above will be substantially stoichiometric unless otherwise specified. In the following examples, reaction concentrations were generally held at 0.1M to the reactants unless a higher concentration or dilution would be particularly useful for influencing the direction of a specific reaction. In practice, amounts will change depending upon variations in reaction conditions and the nature of the reactants.

The examples which follow are set forth to further illustrate various aspects of the present invention, but are not intended to limit its scope in any way.

EXAMPLE 1

Synthesis of 1-(α-N-Boc-L-seryl-O-benzylthioacyl)-2-benzimidazolone a) Preparation of α-N-Boc-L-seryl-O-benzyl-ortho amino anilide N-Boc-L-serine-O-benzyl ether (8.02 mmol) and ortho-phenylene diamine (11.6 mmol) were well dissolved in dichloromethane (21 ml) at 0° C. and N,N'-dicyclohexylcarbodiimide (DCC) (8.27 mmol) added. The mixture was stirred for 1 hour at constant ice temperature and then filtered. The filtrate was transferred to a separating funnel and washed successively with saturated brine/5% aqueous citric acid and saturated brine/5% aqueous sodium bicarbonate followed by saturated brine alone. The organic phase was then dried, concentrated, and the residue purified by flash chromatography on silica gel employing a 3:1 hexane-ethyl acetate solvent as an eluant to yield the α-N-Boc-L-seryl-O-benzyl-ortho amino anilide as a solid in high yield (97%) which was then recrystallized to analytical purity with a dichloromethane-pentane mixture. The compound was observed to have the following physical properties: Melting point 60°-63° C.; $[a]_D^{20}$ (CHCl$_3$) −0.9; UV(CH$_3$CN) lambda$_{max}$ 293; Elemental composition (C$_{21}$N$_{27}$N$_{3/}$O$_4$): Theoretical: C, 65.43; H, 7.06; N, 10.89. Found: C, 65.82; H, 7.42: N, 10.60.

Using the method of preparation described hereinabove and the appropriate starting materials, these additional ortho-amino anilides were synthesized:

a1. α-N-Boc-L-alanyl-ortho-amino anilide
a2. α-N-Boc-L-arginyl-di-N-Cbz-ortho-amino
a3. α-N-Boc-L-arginyl-N-tosyl-ortho-amino
a4. α-N-Boc-L-asparaginyl-N-xanthenyl-ortho-amino anilide
a5. α-N-Boc-L-aspartyl-β-benzyl ester-ortho-amino anilide
a6. α-N-Fmoc-L-aspartyl-β-t-butyl ester-ortho-amino anilide
a7. α-N-Boc-L-cysteinyl-S-benzyl ether-ortho-amino anilide
a8 α-N-Boc-L-glutamyl-γ-benzyl ester-ortho-amino anilide
a9. α-N-Boc-L-glutaminyl-N-xanthenyl-ortho-amino anilide
a10. α-N-Boc-glycyl-ortho-amino anilide
a11. α-N-Boc-L-histidyl-N-benzyl-ortho-amino anilide
a12. α-N-Boc-L-histidyl-N-tosyl-ortho-amino anlide
a13. α-N-Boc-L-isoleucyl-ortho-amino anilide
a14. α-N-Boc-L-leucyl-ortho-amino anilide
a15. α-N-Boo-ε-N-2ClZ-L-lysyl-ortho-amino anilide
a16. α-N-Boo-L-methionyl-ortho-amino anilide
a17. α-N-Boc-L-phenylalanyl-ortho-amino anilide
a18. α-N-Boc-L-prolyl-ortho-amino anilide
a19. α-N-Boc-L-threonyl-O-benzyl ether-ortho-amino anilide
a20. α-N-Boc-L-tryptophyl-ortho-amino anilide
a21. α-N-Boc-L-tyrosinyl-O-2,6-dichlorobenzyl ether-ortho-amino anilide
a22. α-N-Boc-L-valyl-ortho-amino anilide Physical characterizations of these compounds are set forth in Table A.

b) Synthesis of
α-N-Boc-L-seryl-O-benzyl-orthoaminothioanilide

To freshly distilled tetrahydrofuran (THF) (67 ml) was added phosphorous pentasulfide (6.26 mmol) and anhydrous sodium carbonate (6.26 mmol). The mixture was permitted to stir at 20° C. for 0.3 hours. The mixture was then cooled to 0° C. followed by the addition of the N-Boo-L-seryl-O-benzyl-ortho-amino anilide (of step a) (0.71 mmol). After standing at 0° C. for 5-6 hours, 10% aqueous sodium phosphate (tribasic; 22 ml) was added slowly followed by ethyl acetate (20 ml) and hexane (10 ml). The organic phase was separated, washed with brine, dried, and concentrated to yield an oil that was purified by flash chromatography on silica gel using a 6:1:2 hexane-ethyl acetate-methylene chloride solvent mixture as the eluant to give the N-Boc-L-seryl-O-benzyl-ortho-amino thioanilide as a crystalline solid in a moderate yield (50%). The compound was observed to have the following characteristics: Melting point 40°-43° C.; $[a]_D^{20}$ (CHCl$_3$) −26.5; UV (CH$_3$CN) lambda$_{max}$ 271; Elemental composition (C$_{21}$H$_{27}$N$_3$O$_4$): Theoretical: C, 62.82; H, 6.80; N, 10.48; S, 7.98. Found: C, 63.06; H, 7.06; N, 10.42; S, 8.23.

Using the method of preparation described hereinabove and the appropriate starting materials, these additional ortho amino thioanilides were synthesized:

b1. α-N-Boc-L-alanyl-ortho-amino thioanilide
b2. α-N-Boc-L-arginyl-di-N-Cbz-ortho-amino thioanilide
b3. α-N-Boc-L-arginyl-N-tosyl-ortho-amino thioanilide
b4. α-N-Boc-L-asparaginy-N-xanthenyl-ortho-amino thioanilide
b5. α-N-Boc-L-aspartyl-β-benzyl ester-ortho-amino thioanilide
b6. α-N-Fmoc-L-aspartyl-β-t-butyl ester-ortho-amino thioanilide
b7. α-N-Boc-L-cysteinyl-S-benzyl ether-ortho-amino thioanilide
b8. α-N-Boc-L-glutamyl-γ-benzyl ester-ortho-amino thioanilide
b9. α-N-Boc-L-glutaminyl-N-xanthyenl-ortho-amino thioanilide
b10. α-N-Boc-glycyl-ortho-amino thioaniide
b11. α-N-Boc-L-histidyl-N-benzyl-ortho-amino thioanilide
b12. α-N-Boc-L-histidyl-N-tosyl-ortho-amino thioanilide
b13. α-N-Boc-L-isoleucyl-ortho-amino thioanilide
b14. α-N-Boc-L-leucyl-ortho-amino thioanilide
b15. c-N-Boc-s-N-2ClZ-L-lysyl-ortho-amino thioanilide
b16. α-N-Boc-L-methionyl-ortho-amino thioanilide
b17. α-N-Boc-L-phenylalanyl-ortho-amino thioanilide
b18. α-N-Boc-L-prolyl-ortho-amino thioanilide
b19. α-N-Boc-L-threonyl-O-benzy ether-ortho-amino thioanilide
b20. α-N-Boc-L-tryptophyl-ortho-amino thioanilide
b21. α-N-Boc-L-tyrosinyl-O-2,6-dichlorobenzyl ether-ortho-amino thioanilide
b22. α-N-Boc-L-valyl-ortho-amino thioanilide Physical characterizations of these compounds are set forth in Table B.

c) Synthesis of
1-(α-N-Box-L-seryl-O-benzyl-thioacyl)-2-benzimidazalone

The α-N-Boc-L-seryl-O-benzyl-ortho amino thioanilide (of step b) (3.11 mmol) and carbonyl ditriazole (4.36 mmol) were dissolved in THF (45 ml) and after stirring at 25° C. for 6.5 hours, the solvent was removed in vacuo. The residue that remained was dissolved in dichloromethane (2 ml) and purified by flash chromatography. The product was eluted with 4:1 hexane-ethyl acetate to give pure 1-(N-Boc-L-seryl-O-benzyl-2-thioacyl)-2-benzimidazolone in high yield (91%). The compound was characterized by proton NMR and the following physical characteristics were also recorded: Meting point 119°-122° C.; $[a]_D^{20}$ (CHCl$_3$) −25.5; UV (CH$_3$CN) lambda$_{max}$ 265; Elemental Composition (C$_{22}$H$_{25}$N$_3$O$_4$S): Theoretical: C, 61.81; H, 5.90; N, 9.82; S, 7.50. Found: C, 62.00; H, 6.01; N, 10.18; S, 7.30.

Using the method of preparation described hereinabove and the appropriate starting materials, these 1-(α-amino acid thioacyl)-2-benzimidazolone derivatives were synthesized:

c1. 1-(α-Boc-L-alanyl-thioacyl)-2-benzimidazolone
c2. 1-(α-Boc-L-arginyl-di-N-Cbz-thioacyl)-2-benzimidazolone c3. 1-(α-Boc-L-arginyl-N-tosyl-thioacyl)-2-benzimidazolone c4. 1-(α-Boc-L-asparaginyl-N-xanthenylthioacyl)-2-benzimidazolone c5. 1-(α-Boc-L-aspartyl-β-benzyl ester-thioacyl)-2-benzimidazolone c6. 1-(α-Fmoc-L-aspartyl-β-benzyl ester-thioacyl)-2-benzimidazolone c7. 1-(α-Boc-L-cysteinyl-S-benzyl ether-thioacyl)-2-benzimidazolone c8. 1-(α-Boc-L-glutamyl-γ-benzyl ester-thioacyl)-2-benzimidazolone c9. 1-(α-Boc-L-glutaminyl-N-xanthenyl-thioacyl)-2-benzimidazolone c10. 1-(α-Boc-glycyl-thioacyl)-2-benzimidazolone c11. 1-(α-Boc-L-histidyl-N-benzyl-thioacyl)-2-benzimidazolone c12. 1-(α-Boc-L-histidy-N-tosyl-thioacyl)-2-benzimidazolone c13. 1-(α-Boc-L-isoleucyl-thioacyl)-2-benzimidazolone c14. 1-(α-Boc-L-leucyl-thioacyl)-2-benzimidazolone c15. 1-(α-Boc-L-lysyl-ε-N-Cbz-thioacyl)-2-benzimidazolone c16. 1-(α-Boc-L-methionyl-thioacyl)-2-benzimidazolone c17. 1-(α-Boc-L-phenylalanyl-thioacyl)-2-benzimidazolone c18. 1-(α-Boc-L-prolyl-thioacyl)-2-benzimidazolone c19. 1-(α-Boc-L-threonyl-O-benzyl ether-thioacyl)-2-benzimidazolone c20. 1-(α-Boc-L-tryphophyl-1-thioacyl)-2-benzimidazolone c21. 1-(α-Boc-L-tyrosinyl-O2,6-dichlorobenzyl ether-thioacyl)-2-benzimidazolone c22. 1-(α-Boc-L-valyl-thioacyl)-2-benzimidazolone Physical characterizations of these compounds are set forth in Table C.

EXAMPLE 2

Synthesis of 4-Thiothymopentin a) Solution Synthesis i) Preparation of a-N-Boc-L-valyl-L-tyrosyl-O-benzyl-benzyl ester-thioamide α-N-Boc-L-tyrosyl-O-benzyl ether-benzyl ester was treated with trifluoroacetic acid (TFA) at 0° C. under nitrogen for 0.5 hours. The TFA was removed in vacuo to yield L-tyrosyl-O-benzyl-ether-benzyl ester TFA salt. This amino acid derivative was mixed in dichloromethane and treated with 5% aqueous sodium bicarbonate. The organic phase was separated, dried, and concentrated to give the free amino derivative in quantitive yield.

L-tyrosyl-O-2,6 dichlorobenzyl ether benzyl ester (2 mmol) was dissolved in anhydrous N,N'-dimethylformamide (DMF) (0.5 ml) at 0° C. under $N_2$ and 1-(α-N-Boc-valyl-thioacyl)-2-benzimidazolone (2.2 mmol) (from Example 1) was added in portions at 0° C. with stirring over a 0.3 hour period. The mixture was stirred continuously at 0° C. for 2 hours and allowed to warm to 25° C. for 15–17 hours. The reaction was then filtered, concentrated in vacuo, the residue dissolved in ethyl acetate (15 ml) and the solution washed successively with 5% aqueous sodium bicarbonate, water, 5% aqueous citric acid, and water. The organic phase was then dried followed by evaporation and the residue placed on a flash column for purification. The protected dithiopeptide was eluted with a 3:2 ethyl acetate-hexane solvent mixture to afford α-N-Boc-L-valyl-L-tyrosyl-O-benzyl thioamide in good yield (80%). The compound was found to have the following physical characteristics: Melting point 56°–58° C.; IR ($CHCl_3$) 2972, 1735, 1500 cm$^{-1}$; UV ($CHCl_3$) lambda$_{max}$ 272.

ii) Preparation of α-N-Boc-L-aspartyl-β-benzyl ester-L-valyl-L-tyrosyl-O-benzyl ether-benzyl ester-3-thioamide α-N-Boc-L-valyl-L-tyrosyl-O-benzyl thioamide (compound from (i)) was treated with TFA at 0° C. for 0.5 hours under nitrogen to afford, after concentration in vacuo, L-valyl-L-tyrosyl-O-benzyl thioamide TFA salt. The compound was mixed in dichloromethane and treated with 5% aqueous sodium bicarbonate. The organic phase was separated, dried, and concentrated to give the free amino derivative in quantitive yield.

L-valyl-L-tyrosyl-O-benzyl-thioamide (2 mmol) was dissolved in anhydrous DMF (0.5 ml) at 0° C. under $N_2$ and α-N-Boc-L-aspartyl-β-benzyl ester (2 mmol) was added to the solution with stirring. HOBt (2 mmol) and DCC (2 mmol) were added slowly at 0° C. and stirring was allowed to continue overnight. The mixture was diluted with 8 volumes of ethyl acetate and the N,N'-dicyclohexylurea so formed was filtered away from the solution. The filtrate was transferred to a separatory funnel and washed successively with 5% aqueous sodium bicarbonate, 5% aqueous citric acid, and saturated brine. The organic phase was collected and dried over $MgSO_4$, filtered and concentrated in vacuo. The residue was purified by flash chromatography on silica gel employing a 1:1 hexane-ethyl acetate solvent mixture as an eluant to afford the α-N-Boo-L-aspartyl-β-benzyl ester-L-valyl-L-tyrosyl-O-benzyl ether-benzyl ester-3-thioamide in good yield (74%). The following physical characteristics were recorded for the compound: Melting point 112°–114° C. and UV ($CHCl_3$) lambda$_{max}$ 271.

iii) Preparation of α-N-Boc-ε-N-2ClZ-L-lysyl-L-aspartyl-β-benzyl ester-L-valyl-L-tyrosyl-O-benzyl ether-benzyl ester-L-3-thioamide α-N-Boc-L-aspartyl-β-benzyl ester-L-valyl-L-tyrosyl-O-benzyl ether-benzyl ester-2-thioamide (compound from (ii)) was treated with TFA to remove the Boc group as in (ii) and L-aspartyl-β-benzyl ester-L-valyl-L-tyrosyl-O-benzyl ether-benzyl ester-2-thioamide was obtained in quantitive yield.

L-aspartyl-β-benzyl ester-L-valyl-L-tyrosyl-O-benzyl ether-benzyl ester-3-thioamide was dissolved in dry DMF (0.5 ml) at 0° C. under $N_2$ and a-N-Boc-ε-2ClZ-L-lysine (2 mmol) was added to the solution with stirring. HOBt (2 mmol) and DCC (2 mmol) were added slowly at 0° C. and stirring was allowed to continue overnight. The mixture was diluted with 8 volumes of ethyl acetate and the N,N'-dicyclohexylurea so formed was filtered away from the solution. The filtrate was transferred to a separating funnel and washed successively with 5% aqueous sodium bicarbonate, 5% aqueous citric acid, and saturated brine. The organic phase was collected and dried over $MgSO_4$, filtered, and concentrated in vacuo. The residue was purified by flash chromatography on silica gel using a 1:1 hexane-ethyl acetate solvent mixture as an eluant to afford the a-N-Boc-ε-N-2ClZ-L-lysyl-L-aspartyl-β-benzyl ester-L-valyl-L-tyrosyl-O- benzyl ether-benzyl ester-3-thioamide in good yield (73%). The following physical characteristics were recorded for the compound: Melting point 71°–73° C. and UV (CHCl$_3$) lambda$_{max}$ 272.

iv) Preparation of α-N-Boc-N-tosyl-L-arginyl-ε-N-2ClZ-L-lysyl-L-aspartyl-β-benzyl ester-L-valyl-L-tyrosyl-O-benzyl ether-benzyl ester-4-thioamide α-N-Boc-ε-N-2ClZ-L-lysyl-L-aspartyl-β-benzyl ester-L-valyl-L-tyrosyl-O-benzyl ether-benzyl ester-3-thioamide (Compound from (iii)) was treated with TFA to remove the Boc group as in (ii) and ε-N-2ClZ-L-lysyl-L-aspartyl-β-benzyl ester-L-valyl-L-tyrosyl-O-benzyl ether-benzyl ester-3-thioamide was obtained in guantitive yield.

ε-N-2ClZ-L-lysyl-L-aspartyl-β-benzyl ester-L-valyl-L-tyrosyl-O-benzyl ether-benzyl ester-3-thioamide (2 mmol) was dissolved in dry DMF (0.5 ml) at 0° C. under N$_2$ and α-N-Boc-N-tosyl-L-arginine (2 mmol) was added to the solution with stirring. HOBt (2 mmol) and DCC (2 mmol) were added slowly at 0° C. and stirring was allowed to continue overnight. The mixture was diluted with 8 volumes of ethyl acetate and the N,N'-dicyclohexylurea so formed was filtered away from the solution. The filtrate was transferred to a separating funnel and washed successively with 5% aqueous sodium bicarbonate, 5% aqueous citric acid, and saturated brine. The organic phase was collected and dried over MgSO$_4$, filtered, and concentrated in vacuo. The residue was purification by flash chromotography using 9:1 chloroform-methanol as an eluant to afford the α-N-Boc-N-tosyl-L-arginyl-ε-N-2ClZ-L-lysyl-L-aspartyl-β-benzyl ester-L-valyl-L-tyrosyl-O-benzyl ether-benzyl ester-4-thioamide in good yield (78%). The following physical characteristics were recorded for the compound: Melting point 105°–107° C.; IR (CHCl$_3$) 1756, 1%90 cm$^{-1}$ UV (CHCl$_3$) lambda$_{max}$ 271. Elemental composition (C$_{71}$H$_{84}$Cl$_3$N$_9$O$_{14}$S$_2$): Theoretical: C, 58.13; H, 5.65; N, 8.34; S, 4.79. Found: C, 58.54; H, 5.81; N, 8.65; S, 4.40.

v) Preparation of 4-Thiothymopentin

α-N-Boc-N-tosyl-L-arginyl-L-lysyl-ε-N-2ClZ-L-aspartyl-β benzyl ester-L-valyl-L-tyrosyl-O-benzyl ether-benzyl ester-4-thioamide was dissolved in liquid hydrogen fluoride containing 10% by volume of anisole, ethyl methyl sulfide, and thioanisole. After 1 hour at 0° C., the solvent was evaporated in vacuo and the deprotected thiopeptide was purified by reversed phase chromotography on a Vydac C$_{18}$ column utilizing 12% aqueous acetic acid as an eluant. The thiopeptide was characterized by proton NMR and was also found to possess the following physical properties: Melting point 146°–148° C.: UV (CHCl$_3$) lambda$_{max}$ 268; M/e 696.

Using the appropriate sequence of amino acid condensation reactions, the following mono-thiothymopentin analogs were prepared:

d1. L-arginyl-L-lysyl-L-aspartyl-L-valyl-L-tyrosine-1-thioamide d2. L-arginyl-L-lysyl-L-aspartyl-L-valyl-L-tyrosine-2-thioamide d3. L-arginyl-L-lysyl-L-aspartyl-L-valyl-L-tyrosine-3-thioamide Physical characterizations for these thiopeptides are described in Table D.

b) Solid Phase Synthesis i) Preparation of α-N-L-Boo-L-valyl-L-tyrosyl-O-benzyl-thioamide-resin ester α-N-Boc-L-tyrosyl-O-benzyl ether attached to a benzyloxy group of a Merrified resin was treated with a 55% dichloromethane solution of TFA at room temperature for 1 hour. The resin was then collected, washed successively with four portions of 10 ml dichloromethane, four portions of 10 ml isopropanol (IPA) and dried for subsequent use.

L-tyrosyl-O-benzyl ether attached to a benzyloxy group of a Merrifield resin (0.632 mmol/g of resin) was added to a solution of 1-(α-N-Boc-valyl-thioacyl)-2-benzimidazolone (0.948 mmol) in dry DMF (7 ml) with stirring at 25° C. The reaction was stirred for 16 hours after which time another portion of the benzimidazolone (0.948 mmol) was added and stirring was resumed for 18 hours. The resin was collected, washed with four 10 ml portions of DMF, then four 10 ml portions of IPA and subseqently dried in preparation for further reaction.

ii) Preparation of α-N-L-Boo-L-aspartyl-β-benzyl ester-L-valyl-L-tyrosyl-O-benzyl-1-thioamide-resin ester α-N-Boo-L-valyl-L-tyrosyl-O-benzyl ether-thioamide attached to a benzyloxy group of a Merrified resin was treated with a 55% dichloromethane solution of TFA at room temperature for 1 hour. The resin was then collected, washed successively with four portions of 10 ml dichloromethane and four portions of 10 ml iso propyl alcohol (IPA) and dried for subsequent use.

L-valyl-L-tyrosyl-O-benzyl ether-thioamide attached to a benzyloxy group of Merrifield resin (0.632 mmol/g of resin) was added to a solution of α-N-Boc-L-aspartyl-β-benzyl ester (0.632 mmol) in DMF (7 ml) with stirring at 25° C. HOBt (0.632 mmol) and DCC (0.632 mmol) were added slowly with stirring. Reaction was allowed to proceed for 1–2 hours after which time the resin was collected, washed with four 10 ml portions of DMF, four 10 ml portions of IPA, and dried for further reaction.

iii) Preparation of α-N-Boc-s-N-2ClZ-L-lysyl-L-aspartyl-β-benzyl ester-L-valyl-L-tyrosyl-O-benzyl-3-thioamide-resin ester α-N-Boc-L-aspartyl-β-benzyl ester-L-valyl-L-tyrosyl-O-benzyl ether-2-thioamide attached to a benzyloxy group of a Merrified resin was treated with a 55% dichloromethane solution of TFA at room temperature for 1 hour. The resin was then collected, washed successively with four portions of 10 ml dichloromethane and four portions of 10 ml IPA and dried for subsequent use.

L-aspartyl-β-benzyl ester-L-valyl-L-tyrosyl-O-benzyl ether-2-thioamide attached to a benzyloxy group of a Merrifield resin (0.632 mmol/g of resin) was added to a solution of α-N-Boc-N-ε-2ClZ-L-lysine (0.632 mmol) in DMF (7 ml) with stirring and the reaction proceeded for 1–2 hours. The resin was then collected, washed with four 10 ml portions of DMF, four 10 ml portions of IPA, and dried for further reaction.

iv) Preparation of α-N-Boc-N-tosyl-L-arginyl-L-lysyl-ε-N-2ClZ-L-aspartyl-β-benzyl ester-L-valyl-L-tyrosyl-O-benzyl-4-thioamide-resin ester α-N-Boc-ε-N-2ClZ-L-lysyl-L-aspartyl-β-benzyl ester-L-valyl-L-tyrosyl-O-benzyl ether-3-thioamide attached to a benzyloxy group of Merrified resin was treated with a 55% dichloromethane solution of TFA at room temperature for 1 hour. The resin was then collected, washed successively with four portions of 10 ml dichloromethane and four portions of 10 ml IPA and dried for subsequent use.

ε-N-2ClZ-L-lysyl-L-aspartyl-β-benzyl ester-L-valyl-L-tyrosyl-O-benzyl ether-3-thioamide attached to a benzyloxy group of a Merrified resin (0.632 mmol/g of resin) was added to a solution of α-N-Boc-N-tosyl-L-arginine (0.632 mmol) in DMF (7 ml) with stirring at 25° C. HOBt (0.632 mmol) and DCC (0.632 mmol) were added slowly with stirring. Reaction was allowed to proceed for 1-2 hours. The resin was subsequently collected, washed with four 10 ml portions of IPA, and dried for final protecting group removal.

v) Preparation of 1-Thiothymopentin by Removal from Resin

α-N-Boc-N-tosyl-L-arginyl-ε-2ClZ-L-lysyl-L-aspartyl-β-benzyl ester-L-valyl-L-tyrosyl-O-benzyl ether-4-thioamide attached to a benzyloxy group of a Merrifield resin (0.5 mmol) was treated with liquid-hydrogen fluoride (5 ml) containing anisole, dimethyl sulfide, and thioanisole (0.5 ml 1:1:1 v/v) at 0° C. for 1 hour. After evaporation of the solvent, the residue was dissolved in 10% aqueous acetic acid. The aqueous solution was washed with diethyl ether (30 ml), eluted with water and lyophilized to dryness. The crude thiopeptide was dissolved in 92% aqueous acetic acid (25 ml) and purified by reverse phase chromatography employing a $C_{18}$ packed column and the same acetic acid solvent as the eluant.

EXAMPLE 3

Preparation of 3-Thiotuftsin a) Solution Synthesis i) Synthesis of α-N-Boc-L-prolyl-N-tosyl-L-arginyl-benzyl ester thioamide

α-N-Boc-N-tosyl-L-arginyl-benzyl ester was treated with TFA at 0° C. under nitrogen for 0.5 hours. The TFA was removed in vacuo to yield N-tosyl-L-arginyl-benzyl ester TFA salt. This amino acid derivative was mixed in dichloromethane and treated with 5% aqueous sodium bicarbonate. The organic phase was separate, dried, and concentrated to give the free amino derivative in quantitive yield.

N-tosyl-L-arginyl-benzyl ester (2 mmol) was dissolved in anhydrous DMF (0.5 ml) at 0° C. under $N_2$ and 1-(α-N-Boc-L-thioprolyl)-2-benzimidazolone (2.2 mmol) (from Example 1) was added portionwise at 0° C. with stirring over a 0.3 hour period. The mixture was stirred at 0° C. continuously for 2 hours and permitted to warm to 25° C. for 15-17 hours. The reaction was then filtered, concentrated in vacuo, the residue dissolved in ethyl acetate (15 ml) and the solution washed successively with 5% aqueous sodium bicarbonate, water, 5% aqueous citric acid, and water. The organic phase was then dried followed by evaporation and the residue placed on a flash column for purification. The protected thiodipeptide was eluted with a 3:2 ethyl acetate-hexane solvent mixture to afford α-N-Boc-L-thioprolyl-N-tosyl-L-arginyl-benzyl ester in high yield.

The recovered compound possessed the following physical characteristics: Melting point 64°-66° C. and UV ($CHCl_3$) lambda$_{max}$ 270.

ii) Synthesis of α-N-Boc-ε-N-2ClZ-L-lysyl-L-prolyl-N-tosyl-L-arginyl-benzyl ester-2-thioamide α-N-Boo-L-thioprolyl-N-tosyl-L-arginyl-benzyl ester was treated with TFA at 0° C. under nitrogen for 0.5 hours. The TFA was removed in vacuo to yield L-thioprolyl-N-tosyl-L-arginyl-benzyl ester TFA salt. This thiodipeptide was mixed in dichloromethane and treated with aqueous sodium bicarbonate. The organic phase was separated, dried, and concentrated to give the free amino derivative in quantitive yield.

L-thioprolyl-N-tosyl-L-arginyl-benzyl ester (2 mmol) was dissolved in anhydrous DMF (0.5 ml) at 0° C. under $N_2$ and α-N-Boc-ε-N-2ClZ-lysine (2 mmol) was added. HOBt (2 mmol) and DCC (2 mmol) were added slowly with stirring at 0° C. and the reaction was allowed to continue overnight. The reaction was diluted with 8 volumes of ethyl acetate and the N,N'-dicyclohexylurea so formed was filtered away from the mixture. The filtrate was transferred to a separatory funnel and washed successively with 5% aqueous sodium bicarbonate, 5% aqueous citric acid, and saturated brine. The organic phase was collected and dried over $MgSO_4$, filtered and concentrated in vacuo. The residue was purified by flash chromatography on silica ge employing 1:1 hexane-ethyl acetate as an eluant to afford the α-N-Boc-ε-N-2ClZ-L-lysyl-L-prolyl-N-tosyl-L-arginyl-benzyl ester-2-thioamide in high yield.

The following physical characteristics were observed for the purified compound: Melting point 77°-80° C.; IR ($CHCl_3$) 1758, 1380 cm$^{-1}$; UV ($CHCl_3$) lambda$_{max}$ 271; Elemental composition ($C_{55}H_{71}ClN_8O_{11}S_2$): Theoretical: C, 60,75; H, 7.10; N, 9.29. Found: C, 60.34; H, 7.07; N, 9.65.

iii) Synthesis of α-N-Boc-L-threonyl-O-benzyl ether-ε-N-2ClZ-L-lysyl-L-prolyl-N-tosyl-L-arginyl-benzyl ester-3-thioamide α-N-Boc-ε-N-2ClZ-lysyl-L-prolyl-N-tosyl-L-arginyl-benzyl ester-2-thioamide was treated with TFA at 0° C. under nitrogen for 0.5 hours. The TFA was removed in vacuo to yield ε-N-2ClZ-L-lysyl-L-prolyl-N-tosyl-L-arginyl-benzyl ester-2-thioamide TFA salt. This amino acid derivative was mixed in dichloromethane and treated with aqueous sodium bicarbonate. The organic phase was separated, dried, and concentrated to give the free amino derivative in quantitative yield.

ε-N-2ClZ-L-lysyl-L-prolyl-N-tosyl-L-arginyl-benzyl ester-2-thioamide (2 mmol) was dissolved in anhydrous DMF (0.5 ml) at 0° C. under $N_2$ and α-N-Boc-threonine-O-benzyl ether (2 mmol) was added. HOBt (2 mmol) and DCC (2 mmol) were added portion-wise with stirring at 0° C. and the reaction was allowed to continue overnight. The reaction was diluted with 8 volumes of ethyl acetate and the N,N'-dicyclohexylurea so formed was filtered away from the solution. The filtrate was transferred to a separatory funnel and washed successively with 5% aqueous sodium bicarbonate, 5% aqueous citric acid, and saturated brine. The organic phase was collected and dried over MgSO₄, filtered, and concentrated in vacuo. The residue was purified by flash chromatography on silica gel employing a 1:1 hexane-ethyl acetate solvent mixture as an eluant to afford α-N-Boc-L-threonyl-O-benzyl ether-ε-N-2ClZ-L-lysyl-L-prolyl-N-tosyl-L-arginyl-benzyl ester-3-thioamide in high yield.

iv) Preparation of 3-Thiotuftsin

α-N-Boc-L-threonyl-O-benzyl ether-ε-N-2ClZ-L-lysyl-L-prolyl-N-tosyl-L-arginyl-benzyl ester-1-thioamide was dissolved in liquid hydrogen fluoride containing 10% by volume of anisole, ethyl methyl sulfide, and thioanisole. After 1 hour at 0° C., the solvent was removed in vacuo and the deprotected thiopeptide was purified by reversed phase liquid column chromatography on a Vydac C₁₈ column with 12% aqueous acetic acid as an eluant.

The thiopeptide exhibited the following physical characteristics Melting point 169°-171° C. and UV (50% aqueous ethanol) lambda$_{max}$ 268.

The following mono-thiotuftsin analogs were prepared utilizing the appropriate starting materials and the correct sequence of amino acid coupling reactions:

e1. L-threonyl-L-lysyl-L-prolyl-L-arginine-2-thioamide e2. L-threonyl-L-lysyl-L-prolyl-L-arginine-1-thioamide Physical characterizations for these thiopeptides are described in Table E.

EXAMPLE 4

Evaluation of Thymopentin and 4-Thiothymopentin on T cell Development in Nude Athymic Mice This assay was performed according to the protocol established by Lau and Goldstein. See C. Lau and G. Goldstein, "Functional Effects of Thymopentin on Cytotoxic Lymphocyte Precursor Units", *J. Immun.*, 124, 1861 (1980); and G. Goldstein et a., "T cell Development in Normal and Thymopentin-treated Nude Mice", *J. Exp. Med.*, 156, 1057 (1982).

The immunomodulatory action of thymopentin and 4-thiothymopentin on immature T-cell development by the expression of de novo antigens on T lymphocytes after daily subcutaneous injections for two weeks in four week old nude athymic mice was measured. Following the final injection, the splenocytes were prepared and radio-labelled to determine the percentage of total cells bearing the radio labeled marker. Two distinct sets of experiments established the 4-thiothymopentin as having a 128% and 227% increase of cells bearing these markers over control animals administrered thymopentin at the same concentration and rate, under the same conditions in this assay.

These findings suggest that thiothymopentin analogs can induce a potent differentiation process associated with an increase of cell surface markers of T-lymphocytes.

Many variations and additional embodiments will be readily apparent to those skilled in the art in view of the foregoing disclosures and examples. For example, thiopeptides of greater than five amino acid residues having improved characteristics as described herein, may be advantageously prepared according to the methods of the present invention. All such obvious variations and further embodiments are included within the scope of the appended claims.

TABLE A

| Cmpnd | m.p. °C. | $[α]_D^{20}$ (CHCl₃) | U.V. λmax (CH₃CN) | % C | % H | % N | % S |
|---|---|---|---|---|---|---|---|
| | | | | \multicolumn{4}{c}{(found) / (theoretical)} | | | |
| a1 | 123-25 | −54.5 | 294 (3.75) | 60.23 / 60.20 | 7.77 / 7.58 | 14.76 / 15.03 | |
| a2 | 116-18 | −1.5 | 293 (3.48) | 62.47 / 62.65 | 6.45 / 6.37 | 13.38 / 13.28 | |
| a3 | 101-02 | −17.8 | 295 (3.60) | 55.57 | 6.61 | 16.20 | 6.18 |
| a4 | 222-24 | −10 (THF) | 289 (3.58) | 66.77 / 66.91 | 6.33 / 6.02 | 11.35 / 11.14 | |
| a5 | 100-02 | −13.0 | 292 (3.49) | 64.16 / 63.90 | 7.05 / 6.58 | 10.56 / 10.16 | |
| a6 | 128-30 | 6.4 | 263 (4.13) | 69.33 / 69.44 | 6.48 / 6.23 | 8.48 / 8.37 | |
| a7 | 128-30 | −14.2 | 293 (3.92) | 63.00 / 62.82 | 7.01 / 6.78 | 10.77 / 10.46 | 7.54 / 7.98 |
| a8 | 75-78 | −20.8 | 293 (3.39) | 64.42 / 64.62 | 7.06 / 6.84 | 9.59 / 9.82 | |
| a9 | 212-13 | | 294 (3.43) | 67.59 / 67.43 | 6.54 / 6.24 | 11.14 / 10.84 | |
| a10 | 148-49 | 0 | 293 (3.39) | 58.56 / 58.86 | 7.31 / 7.22 | 15.44 / 15.83 | |
| a11 | 49-52 | −5.2 | 294 (3.44) | 65.90 / 66.19 | 7.11 / 6.71 | 15.65 / 16.07 | |
| a12 | 82-84 | 7.8 | 292 (3.45) | | | | |
| a13 | 150-51 | −38.8 | 294 (3.55) | 63.50 / 63.53 | 8.54 / 8.47 | 13.28 / 13.08 | |
| a14 | 225-27 | −2.5 (THF) | 280 (3.07) | 63.49 / 63.53 | 8.79 / 8.47 | 13.02 / 13.08 | |
| a15 | 94-97 | −26.8 | 293 (3.63) | 59.99 / 59.46 | 6.94 / 6.58 | 10.80 / 11.09 | |
| a16 | 137-38 | −29.0 | 294 (3.15) | 56.49 / 56.61 | 7.69 / 7.42 | 12.11 / 12.39 | 9.34 / 9.44 |
| a17 | 141-42 | 0 | 301 (3.60) | 67.38 / 67.58 | 7.42 / 7.09 | 11.88 / 11.81 | |
| a18 | 164-66 | −105 | 293 (3.52) | 63.31 / 62.93 | 7.90 / 7.59 | 13.61 / 13.75 | |
| a19 | 142-44 | 7.2 | 292 (3.54) | 65.95 / 66.14 | 7.52 / 7.32 | 10.37 / 10.51 | |
| a20 | 149-52 | −2.6 (CH₃CN) | 288 (4.17) | 67.29 / 66.98 | 7.05 / 6.64 | 14.37 / 14.20 | |
| a21 | 173-75 | 20.9 (THF) | 293 (3.56) | 60.70 / 61.14 | 5.67 / 5.51 | 7.62 / 7.92 | |
| a22 | 125-26 | −39.8 | 292 (3.49) | 62.94 / 62.54 | 8.32 / 8.19 | 13.81 / 13.68 | |

TABLE B

| Cmpnd | m.p. °C. | $[α]_D^{20}$ (CHCl₃) | U.V. λmax (CH₃CN) | % C | % H | % N | % S |
|---|---|---|---|---|---|---|---|
| | | | | \multicolumn{4}{c}{(found) / (theoretical)} | | | |
| b1 | 126-28 | −71.4 | 270 (3.96) | 57.14 / 56.92 | 7.27 / 7.17 | 14.48 / 14.22 | 10.96 / 10.85 |
| b2 | 68-70 | −14.6 | 271 (4.06) | 61.08 / 61.09 | 6.48 / 6.21 | 12.92 / 12.95 | 4.70 / 4.94 |
| b3 | 130-37 | −11.3 | 271 (4.23) | 53.66 / 53.91 | 6.80 / 6.41 | 15.51 / 15.71 | 12.33 / 12.00 |
| b4 | 98-99 | 18.9 | 278 (4.12) | 64.81 / 64.84 | 6.05 / 5.83 | 11.14 / 10.80 | 6.19 / 6.18 |
| b5 | 125-26 | −27.9 | 274 (4.16) | 61.12 / 61.52 | 6.19 / 6.29 | 9.39 / 9.78 | 7.34 / 7.46 |
| b6 | 74-78 | −12.8 | 264 (4.21) | 67.13 / 67.29 | 6.47 / 6.04 | 8.45 / 8.12 | 5.92 / 6.19 |
| b7 | 114-15 | −48.0 | 273 (4.06) | 60.30 / 60.40 | 6.58 / 6.52 | 9.86 / 10.06 | 15.02 / 15.35 |
| b8 | 51-53 | −19.4 | 272 (3.75) | 63.08 / 62.58 | 6.80 / 6.59 | 9.39 / 9.47 | 6.96 / 7.23 |
| b9 | 210-11 | −4.5 (THF) | 277 (4.20) | 65.16 / 65.39 | 6.45 / 6.05 | 10.85 / 10.51 | 6.01 / 6.02 |
| b10 | 124-25 | −0.1 | 296 (4.00) | 55.89 / 55.49 | 7.10 / 6.81 | 14.80 / 14.92 | 11.57 / 11.39 |

TABLE B-continued

| Cmpnd | m.p. °C. | $[\alpha]_D^{20}$ (CHCl₃) | U.V. λmax (CH₃CN) | %C (found) / %C (theoretical) | %H (found) / %H (theoretical) | %N (found) / %N (theoretical) | %S (found) / %S (theoretical) |
|---|---|---|---|---|---|---|---|
| b11 | 60–62 | −21.0 | 273 (3.93) | 65.04 / 63.83 | 6.82 / 6.47 | 15.63 / 15.50 | 7.04 / 7.10 |
| b12 | 116–17 | 81.2 | 268 (3.92) | | | | |
| b13 | 139–40 | −6.8 | 273 (4.08) | 60.85 / 60.52 | 8.24 / 8.06 | 12.75 / 12.44 | 9.28 / 9.50 |
| b14 | 66–70 | −42.9 | 273 (3.93) | 60.65 / 60.52 | 8.25 / 8.06 | 12.51 / 12.44 | 9.27 / 9.50 |
| b15 | 56–58 | −34.0 | 272 (3.98) | 58.00 / 57.62 | 6.67 / 6.37 | 11.10 / 10.74 | 6.27 / 6.15 |
| b16 | 46–48 | −6.1 | 273 (3.98) | 53.80 / 54.06 | 6.81 / 7.09 | 11.86 / 11.82 | 17.79 / 18.04 |
| b17 | 66–69 | 41.3 | 273 (4.06) | 65.03 / 64.70 | 7.00 / 6.78 | 16.09 / 11.30 | 8.41 / 8.61 |
| b18 | 73–75 | −179 (c = 0.5) | 270 (4.10) | 60.00 / 59.80 | 7.65 / 7.21 | 13.00 / 13.06 | 9.60 / 9.97 |
| b19 | 49–52 | −34.6 | 272 (3.93) | 63.74 / 63.52 | 7.57 / 7.33 | 9.90 / 10.10 | 7.46 / 7.71 |
| b20 | 161–62 | 19.9 | 273 (4.31) | 64.52 / 64.36 | 6.59 / 6.38 | 13.76 / 13.64 | 7.63 / 7.81 |
| b21 | 164–65 | 39.2 | 273 (4.14) | 59.68 / 59.33 | 5.66 / 5.35 | 7.74 / 7.68 | 5.74 / 5.87 |
| b22 | 117–19 | −7.7 | 273 (4.18) | 59.63 / 59.40 | 7.72 / 7.79 | 12.74 / 12.98 | 10.03 / 9.91 |

TABLE C

| Cmpnd | M.P. °C. | $[\alpha]_D^{20}$ (CHCl₃) | U.V. λmax (CH₃CN) | %C (found) / %C (theoretical) | %H (found) / %H (theoretical) | %N (found) / %N (theoretical) | %S (found) / %S (theoretical) |
|---|---|---|---|---|---|---|---|
| c1 | 103–05 | −19.0 | 263 (3.60) | 55.82 / 56.06 | 5.97 / 5.96 | 12.73 / 13.07 | 10.04 / 9.98 |
| c2 | 152–54 | 3.4 | 263 (4.03) | 60.35 / 60.52 | 5.80 / 5.68 | 12.41 / 12.45 | 4.62 / 4.75 |
| c3 | | | NOT ISOLATED | | | | |
| c4 | 177–81 | 55.2 (DMF) | 264 (3.74) | | | | |
| c5 | | | NOT ISOLATED | | | | |
| c6 | | | NOT ISOLATED | | | | |
| c7 | 136–38 | 46.0 | 266 (3.78) | 59.20 / 59.57 | 5.80 / 5.68 | 9.41 / 9.47 | 14.40 / 14.45 |
| c8 | 124–27 | 48.0 | 264 (3.92) | 61.66 / 61.39 | 6.05 / 5.80 | 8.53 / 8.55 | 7.00 / 6.83 |
| c9 | 132–34 | 53.5 (THF) | 264 (3.79) | 64.54 / 64.80 | 5.80 / 5.41 | 9.83 / 10.02 | 5.96 / 5.74 |
| c10 | 121–24 | 0 | 263 (3.92) | 54.91 / 54.71 | 5.84 / 5.57 | 13.17 / 13.66 | 10.03 / 10.42 |
| c11 | | | NOT ISOLATED | | | | |
| c12 | | | NOT ISOLATED | | | | |
| c13 | 72–73 | 129 | 265 (3.92) | 59.79 / 59.48 | 7.18 / 6.93 | 11.86 / 11.55 | 8.87 / 8.82 |
| c14 | 123–16 | 46.8 | 264 (3.90) | 59.70 / 59.48 | 7.09 / 6.93 | 11.75 / 11.55 | 9.12 / 8.82 |
| c15 | 134–36 | 30.3 | 264 (4.00) | 56.72 / 57.08 | 5.83 / 5.71 | 10.16 / 10.24 | 5.53 / 5.86 |
| c16 | 118–20 | 46.9 | 263 (4.10) | 53.38 / 53.52 | 6.39 / 6.07 | 11.50 / 11.10 | 16.74 / 16.81 |
| c17 | 166–69 | 141.3 | 263 (4.27) | 63.32 / 63.45 | 5.73 / 6.83 | 10.87 / 10.46 | 8.26 / 8.06 |
| c18 | 136–38 | −203 | 266 (3.94) | 58.48 / 58.76 | 6.34 / 6.10 | 12.14 / 12.09 | 9.47 / 9.22 |
| c19 | 138–40 | 43.3 | 266 (4.01) | 62.22 / 62.56 | 6.40 / 6.16 | 9.27 / 9.51 | 7.54 / 7.26 |
| c20 | 164–67 | 146 | 266 (4.08) | 63.55 / 63.28 | 5.81 / 5.54 | 13.00 / 12.83 | 7.29 / 7.34 |
| c21 | 187–89 | 109 | 264 (4.08) | 58.66 / 58.74 | 4.99 / 4.75 | 7.76 / 7.34 | 5.47 / 5.60 |
| c22 | 148–50 | 146 | 266 | 58.79 | 6.94 | 11.86 | 9.11 |

TABLE C-continued

| Cmpnd | M.P. °C. | $[\alpha]_D^{20}$ (CHCl₃) | U.V. λmax (CH₃CN) | %C (found) / %C (theoretical) | %H (found) / %H (theoretical) | %N (found) / %N (theoretical) | %S (found) / %S (theoretical) |
|---|---|---|---|---|---|---|---|
| | | | (3.98) | 58.42 | 6.63 | 12.02 | 9.17 |

TABLE D

| Cmpnd | M.P. °C. | U.V. λmax (CH₃CN) |
|---|---|---|
| d1 | 140–42 | 268 (3.86) |
| d2 | 133–34 | 269 (3.71) |
| d3 | 148–50 | 269 (3.89) |

TABLE E

| Cmpnd | M.P. °C. | U.V. λmax (CH₃CN) |
|---|---|---|
| e1 | 182–83 | 267 (3.81) (in 50% EtOH) |

What is claimed is:

1. A thioacylating reagent of the formula:

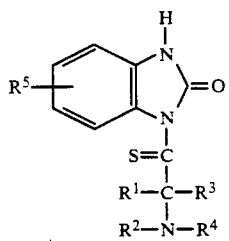

wherein $R^1$ is hydrogen or $C_1$–$C_4$ branched or unbranched alkyl which may be substituted by a substituent selected form the group consisting of:

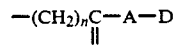

wherein
A is —O— or —NH—,
D is benzyl or xanthenyl,
n is 1 or 2;

wherein
E is —H or —CH₃,
G is —CH₂—, —O— or —S—,
J is —S— or —CH₂—,
L is —CH₃ or phenyl;

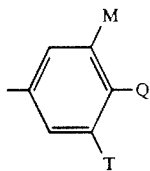

wherein M and T may be the same or different and are members selected from the group consisting of hydrogen, fluorine chlorine, bromine and iodine, and Q is hydrogen, hydroxy, or dichlorobenzoxy;

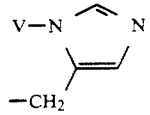

wherein V is carbobenzyloxy or tosyl; or

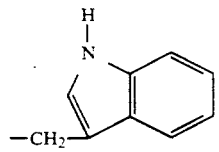

$R^2$ is selected from the group consisting of t-butoxycarbonyl, carbobenzyloxy, chlorobenzyloxy, 9-fluorenylmethoxycarbonyl, tosyl, trityl, and xanthenyl;

$R^3$ is hydrogen, methyl, or ethyl; or $R^1$ and $R^3$, taken together with the carbon atom to which they are attached, form a cycloalkyl group containing 3-5 carbon atoms;

$R^4$ is hydrogen; or $R^1$ and $R^4$, taken together with the carbon and nitrogen atoms to which they are attached, form an aziridine, azetidine, pyrrolidine or piperidine ring; and $R^5$ is selected from the group consisting of hydrogen, methyl, ethyl, fluorine, chlorine, bromine, iodine, amino, amido, azido, hydroxy, hydroxymethyl, carboxy, carboxymethyl, cyano, guanido, mercapto, and nitro.

2. The thioacylating reagent according to claim 1, wherein $R^1$ is $C_1$-$C_4$ branched or unbranched alkyl, $R^2$ is t-butoxycarbonyl, and $R^3$ is hydrogen.

3. The thioacylating reagent according to claim 2, wherein $R^1$ and $R^4$, taken together with the carbon and nitrogen atoms to which they are attached, form a pyrrolidine ring $R^2$ is t-butoxycarbonyl, and $R^3$ and $R^5$ are hydrogen.

4. The thioacylating reagent according to claim 1, wherein R is represented by the formula:

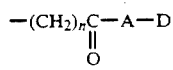

wherein
A is —O— or —NH—,
D is benzyl or xanthenyl,
n is 1 or 2;
$R^2$ is t-butoxycarbonyl; and
$R^3$ and $R^5$ are hydrogen.

5. A compound according to claim 1, wherein $R^1$ is represented by the formula:

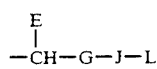

wherein
E is —H or —CH$_3$,
G is —CH2—, —O— or —S—,
J is —S— or —CH$_2$—,
L is —CH$_3$ or phenyl;
$R^2$ is t-butoxycarbonyl; and
$R^3$ and $R^5$ are hydrogen.

6. The thioacylating reagent according to claim 1, wherein $R^1$ is represented by the formula:

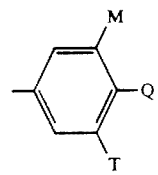

wherein M and T may be the same or different and are substituents selected from the group consisting of hydrogen, flourine, chlorine, bromine and iodine, and Q is hydrogen, hydroxy, or dichlorobenzoxy;
$R^2$ is t-butoxycarbonyl; and
$R^3$ and $R^5$ are hydrogen.

7. The thioacylating reagent according claim 1, wherein $R^1$ is represented by the formula:

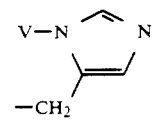

wherein V is carbobenzyloxy or tosyl;
$R^2$ is t-butoxycarbonyl; and
$R^3$ and $R^5$ are hydrogen.

8. The thioacylating reagent according to claim 1, wherein R is:

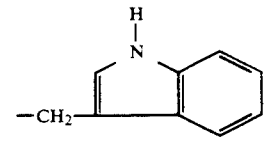

$R^2$ is t-butoxycarbonyl; and
$R^3$ and $R^5$ are hydrogen.

9. The thioacylating reagent according to claim 1, wherein R is represented by the formula:

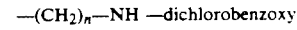

wherein n is 1-4 and $R^3$ and $R^5$ are hydrogen.

10. The thioacylating reagent according to claim 1, wherein $R_1$ is:

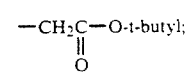

R² is 9-fluorenylmethyloxycarbonyl; and
R³ and R⁵ are hydrogen.

11. A thioacylating reagent wherein the the thioacylating reagent is selected from the group consisting of:

1-(α-Boc-L-alanyl-thioacyl)-2-benzimidazolone, 1-(α-Boc-L-arginyl-di-N-Cbz-thioacyl)-2-benzimidazolone, 1-(α-Boc-L-arginyl-N-tosyl-thioacyl-)-2-benzimidazolone, 1-(α-Boc-L-asparaginyl-N-xanthenyl-thioacyl)-2-benzimidazolone, 1-(α-Boo-L-aspartyl-β-benzyl ester-thioacyl)-2-benzimidazolone, 1-(α-Fmoc-L-aspartyl-β-t-butyl ester-thioacyl)-2-benzimidazolone, 1-(α-Boc-L-cysteinyl-S-benzyl ether-thioacyl)-2-benzimidazolone, 1-(α-Boc-L-glutamyl-γ-benzyl ester-thioacyl)-2-benzimidazolone, 1-(α-Boc-L-glutaminyl-N-xanthenyl-thioacyl)-2-benzimidazolone, 1-(α-Boc-glycyl-thioacyl)-2-benzimidazolone, 1-(α-Boc-L-histidyl-N-benzyl-thioacyl)-2-benzimidazolone, 1-(α-Boc-L-histidyl-N-tosyl-thioacyl)-2-benzimidazolone, 1-(α-Boc-L-isoleucyl-thioacyl)-2-benzimidazolone, 1-(α-Boc-L-lysyl-ε-N-Cbz-thioacyl)-2-benzimidazolone, 1-(α-Boc-L-methionyl-thioacyl)-2-benzimidazolone, 1-(α-Boc-L-phenylalanyl-thioacyl)-2-benzimidazolone, 1-(α-Boc-L-prolyl-thioacyl)-2-benzimidazolone, 1-(α-Boc-L-threonyl-O-benzyl ether-thioacyl)-2-benzimidazolone, 1-(α-Boc-L-tryphophylthioacyl)-2-benzimidazolone, 1-(α-Boc-L-tyrosinyl)-O-2,6-dichlorobenzyl ether-thioacyl)-2-benzimidazolone, or 1-(α-Boc-L-valyl-thioacyl)-2-benzimidazolone.

* * * * *